US008496874B2

United States Patent
Gellman et al.

(10) Patent No.: US 8,496,874 B2
(45) Date of Patent: Jul. 30, 2013

(54) INTEGRATED CENTRIFUGAL BLOOD PUMP-OXYGENATOR, AN EXTRACORPOREAL LIFE SUPPORT SYSTEM AND A METHOD OF DE-BUBBLING AND PRIMING AN EXTRACORPOREAL LIFE SUPPORT SYSTEM

(75) Inventors: Barry N. Gellman, North Easton, MA (US); Andrew Koert, Somerville, MA (US); Zhongjun Wu, Woodstock, MD (US); Juntao Zhang, Baltimore, MD (US); Bartley P. Griffith, Gibson Island, MD (US)

(73) Assignee: Thoratec LLC, Pleasanton, CA (US)

( * ) Notice: Subject to any disclaimer, the term of this patent is extended or adjusted under 35 U.S.C. 154(b) by 756 days.

(21) Appl. No.: 11/999,707

(22) Filed: Dec. 5, 2007

(65) Prior Publication Data

US 2008/0199357 A1 Aug. 21, 2008

Related U.S. Application Data

(60) Provisional application No. 60/873,468, filed on Dec. 7, 2006.

(51) Int. Cl.
*A61M 1/00* (2006.01)
*A61M 37/00* (2006.01)

(52) U.S. Cl.
USPC ............. 422/45; 422/44; 422/46; 422/47; 422/48; 604/4.01; 604/5.01; 604/6.09; 604/6.11; 604/6.13; 604/6.14

(58) Field of Classification Search
USPC ............. 422/44–48; 604/4.01, 6.09, 6.11, 604/6.13, 6.14
See application file for complete search history.

(56) References Cited

U.S. PATENT DOCUMENTS

| 4,975,247 | A | | 12/1990 | Badolato et al. | |
|---|---|---|---|---|---|
| 5,240,677 | A | * | 8/1993 | Jones et al. | 422/46 |
| 5,270,005 | A | | 12/1993 | Raible | |
| 5,501,663 | A | | 3/1996 | Hattler | |
| 6,155,969 | A | * | 12/2000 | Schima et al. | 600/16 |
| 6,630,107 | B1 | * | 10/2003 | Merce Vives | 422/45 |
| 6,730,267 | B2 | * | 5/2004 | Stringer et al. | 422/45 |

FOREIGN PATENT DOCUMENTS

WO WO 02/064013 A2 8/2002
WO 02/100475 A1 12/2002

* cited by examiner

*Primary Examiner* — Leslie Deak
(74) *Attorney, Agent, or Firm* — Kilpatrick Townsend & Stockton LLP

(57) ABSTRACT

An integrated centrifugal blood pump-oxygenator (1) which has a housing (2) with a top (3) having a blood inlet (4), a blood outlet (5) and a gas inlet (6), and a bottom (7) having a rotational body (8) being rotatably arranged in a rotor-housing (9) of the bottom (7). The integrated centrifugal blood pump-oxygenator (1) further has an oxygenator membrane (10) provided in an interior (11) of the housing (2), wherein in the operation state oxygen (12) is transferred from the gas inlet (6) through the oxygenator membrane (10) to a gas outlet (13) and blood (14) is brought in direct contact with the oxygenator membrane (10) by pumping the blood (14) with the rotational body (8) from the blood inlet (4) to the blood outlet (5). The rotational body (8) is magnetically journalled in a contact-free manner with respect to the rotor-housing (9). There is an extracorporeal life support system (1000), and a method of de-bubbling and priming a extracorporeal life support system (1000).

47 Claims, 7 Drawing Sheets

INTEGRATED CENTRIFUGAL BLOOD PUMP-OXYGENATOR, AN EXTRACORPOREAL LIFE SUPPORT SYSTEM AND A METHOD OF DE-BUBBLING AND PRIMING AN EXTRACORPOREAL LIFE SUPPORT SYSTEM

CROSS-REFERENCES TO RELATED APPLICATIONS

This application claims the priority of U.S. Patent Application No. 60/873,468, filed Dec. 7, 2006, the disclosure of which is incorporated herein by reference.

STATEMENT OF GOVERNMENT SUPPORT

This work was supported, at least in part, by the National Institutes of Health Small Business Technology Transfer under Grant No. NIH 5R42 HL084807. Therefore, the Government of the United States of America has certain rights in the invention.

FIELD OF THE INVENTION

The invention relates to an integrated centrifugal blood pump-oxygenator, an extracorporeal life support system as well as to a method of de-bubbling and priming an extracorporeal life support system. In accordance with the invention, the integrated device employs a bearingless magnetically rotating impeller to pump and oxygenate blood. The extracorporeal life support system includes an integrated centrifugal blood pump-oxygenator.

BACKGROUND OF THE INVENTION

Lung disease is the third largest cause of death in the United States of America, accounting for approximately one out of every seven adult deaths. It is estimated that 30 million Americans are living with chronic lung disease. Adult respiratory distress syndrome (ARDS) afflicts approximately 150,000 patients annually in the U.S. Despite advances in critical care, mortality remains around 40-50%.

Currently available therapies for patients with chronic respiratory failure include, for example, ventilation and extracorporeal membrane oxygenation (ECMO). Mechanical ventilation is effective for short-term support. Often, however, the excessive tidal volumes, airway pressure and oxygen fraction necessary to achieve sufficient gas exchange with mechanical ventilation can cause further damage to the lungs, creating ventilator-induced lung injury, including barotrauma, volutrauma and other iatrogenic injuries, further exacerbating acute respiratory insufficiency in many patients. ECMO systems are attractive since they closely simulate physiological gas exchange. However, they are complex in operation, can result in thrombosis, blood trauma, infection and bleeding due to the need for high levels of anti-coagulation, and limit patient mobility. Arteriovenous pumpless oxygenation may benefit some patients with acute lung failure but achievable flow is limited and its use is currently limited to intensive care units (ICU).

There have been efforts to develop more efficient and compact devices for respiratory and cardiopulmonary support systems. For example, attempts have been made to integrate multiple components of cardiopulmonary, ECMO systems into single structures so as to eliminate or minimize the need for the extension of lengthy, blood-filled tubes. Various integrated pump-oxygenators have been described (see, e.g., U.S. Pat. Nos. 5,217,689; 5,266,265; 5,270,005; 5,770,149; 4,975,247; 5,429,486; 6,963,222; and 6,730,267). There are drawbacks associated with these integrated pump-oxygenators, however. Such drawbacks include non-uniform blood flow through the fiber membranes and the existence of laminar boundary flow zones between blood cells and fiber membranes. Non-uniform blood flow across the fiber membranes results in hyper- and hypo-perfusion of the blood in flow paths. Hyper-perfusion does not grant any additional benefit once blood is oxygen-saturated, yet subjects the blood unnecessarily to prolonged exposure to artificial materials, thereby increasing risk of hemolysis and thrombosis. Hyper-perfusion occurs when oxygen-saturated blood is exposed to oxygenator fibers. The exposure to oxygenator fibers does not confer any benefit to the blood because it is already saturated with oxygen. Rather, the exposure unnecessarily increases shear stress and contact with synthetic material. Hypo-perfusion occurs when blood is incompletely saturated with oxygen before it is discharged from the oxygenator. In order to combat hypo-perfusion, longer flow paths and fiber membranes having larger surface areas (e.g. 2-4 $m^2$) are used, resulting in extended contact of the blood with the fiber membrane surfaces, which, in turn, leads to blood activation thrombosis formation.

When the blood is passively pumped to flow through fiber membranes, a relatively thick blood boundary layer forms and impedes diffusion of oxygen to blood cells, which are not in direct contact with the filter membrane surface. Thus, the blood boundary layer significantly hinders gas transfer efficiency.

Therefore, gas exchange membrane surface areas of 2 to 4 $m^2$ are typically required to provide the needed gas exchange for an adult. The bundle sizes utilized in open heart surgery are larger to compensate for the greater oxygen demand that occurs during patient re-warming. This is not critical in ECMO applications as the patient is maintained at normothermic conditions or only slightly less. Consequently, the volume of the devices is impractical for portable deployment. In addition, the pumps used in today's ECMO systems or proposed to be used in the above patents all can lead to device-induced blood trauma (hemolysis, and blood element activation) due to the technologies utilized (mechanical bearings, non-optimized flow paths and large prime volume).

Efforts to decrease the effect of the boundary layer include increasing shear rate and/or turbulence of the blood flow path by the introduction of secondary flows, for example, by directing blood to flow at a substantial angle, such as perpendicular, to the fiber membranes. U.S. Pat. No. 4,639,353, for example, discloses the use of an arrangement of bundles of hollow fibers perpendicular to the direction of blood flow via a series of flow guide structures. U.S. Pat. No. 5,263,924 discloses the use of an integrated centrifugal pump and membrane oxygenator comprising hollow fibers, which are displaced circumferentially in a ring around an impeller of the centrifugal pump and through which blood is pumped for oxygenation. Other efforts to decrease the effect of the boundary layer include actively rotating hollow fiber membranes or moving fiber membranes in the path of blood flow. The motion of membrane surfaces relative to the blood cells causes pumping and oxygenation to occur simultaneously and can disrupt the build-up of the boundary layer around the gas exchange surface. Examples of oxygenators with active gas exchange membranes include those described in U.S. Pat. Nos. 5,830,370; 6,723,284; and 6,503,450; and in the paper by Makarewics et al. (ASAIO 42: M615-619 (1996)).

Despite improvements in the performance and design of conventional blood pump-oxygenators, there remains a need for a more compact and efficient blood pump-oxygenator with less pronounced or fewer drawbacks. Thus, there is a need for a compact, efficient and non-traumatic pump-oxygenator with pumping function, low prime volume and low gas exchange membrane surface area.

SUMMARY OF THE INVENTION

It is an object of the present invention to provide such an improved blood pump-oxygenator. This and other objects and advantages, as well as additional inventive features, will become apparent in the detailed description provided herein.

The invention thus relates to an integrated centrifugal blood pump-oxygenator comprising a housing with a top having a blood inlet, a blood outlet, and a gas inlet, and a bottom having a rotational body being rotatably arranged in a rotor-housing of the bottom. The integrated centrifugal blood pump-oxygenator further comprises an oxygenator membrane provided in an interior of the housing, wherein in the operation state oxygen is transferred from the gas inlet through the oxygenator membrane to an gas outlet and blood is brought in direct contact with the oxygenator membrane by pumping the blood from the blood inlet to the blood outlet with the rotational body. According to the invention, the rotational body is magnetically journalled in a contact-free manner with respect to the rotor-housing.

Therefore, it is essential for the integrated centrifugal blood pump-oxygenator that the rotational body of the pump-oxygenator is magnetically journalled in a contact-free manner with respect to the rotor-housing.

Conventional rotary pumps with hermetically closed pump housings are used when a complete separation of the fluid to be conveyed from the surroundings is required. Although this requirement would be easily fulfilled for example by hose squeezing pumps rather than by rotary pumps, hose squeezing pumps, so-called peristaltic pumps, or roller pumps can frequently not be used because shear forces act on the fluid during their operation by virtue of their specific construction through which the structure of the fluid is impaired. In pharmaceutical and medical fields of application, in particular those including mechanically sensitive fluids with cells having sensitive cell membranes, it is necessary to use rotary pumps.

In pumping blood, for example, there is the danger that a hemolysis arises as a result of such shear forces, which renders the blood unusable. In contrast to the situation with piston pumps, the fluids are exposed to practically no shear forces in centrifugal pumps so that fluids containing sensitive cells are protected when being conveyed.

Another very important point, in particular regarding medical applications, is a strict material isolation of the fluid to be forwarded. A strict material isolation of the fluid is absolutely necessary in medical applications for two main reasons: On the one hand, an outflow of even the smallest amounts of fluid to the surroundings cannot be tolerated; on the other hand, an intrusion of foreign substances of any kind into the fluid should be prevented when the latter must satisfy the highest requirements with respect to purity, which is certainly the case when using a pump in the medical field. Especially for these fields of application, the material isolation of the fluid, for example blood, must consist in particular in preventing the intrusion of particles abraded from relatively moving components of the drive device, of the bearing arrangement, or of a sealing arrangement. Lubricants should also be prevented from entering into the fluid.

Pumps of the above-named kind are for example used during open heart surgery for maintaining the blood circulation of the patient. It is self-evident that in such cases the highest demands are made with respect to maintaining the purity of the blood.

By using conventional drive devices, bearing devices and sliding ring seals proved impossible to seal off the pump housing completely relative to the surroundings and at the same time to prevent the production of abraded particles from relatively moved components and the intrusion of such abrasion particles and of lubricants into the blood.

These and further drawbacks are well known to those skilled in the art and have been discussed intensively for example by U.S. Pat. No. 6,100,618.

To overcome the aforementioned drawbacks of conventional rotary pumps in medical applications, it has been proposed to use, in particular for medical applications such as for pumping blood during open heart surgery, pumps having a rotor which is magnetically journalled in a contact-free manner with respect to a rotor-housing.

Such electrical rotary drives are preferably, but not necessarily, designed in accordance with U.S. Pat. No. 6,640,617, EP 0 819 330 or EP 1 063 753 as a bearing-free motor with a magnetically journalled rotor and a stator, with the drive and the magnetic support for the rotor forming a unit in accordance with the principle of a bearing-free motor. The stator may have a drive winding with a strand for generating a magnetic drive field which produces a torque on the rotor. The magnetic drive field is in this connection preferably controlled by a torque-forming current. In addition, the stator has a control winding including at least one strand for generating a magnetic control field with which the position of the rotor with respect to the stator can be regulated via a control current. In an embodiment which is very important in practice, the magnetic drive field and the magnetic control field can be completely uncoupled from one another so that the torque-forming current of the drive winding feeds the total mechanical motor power essentially on its own.

It is understood that in another embodiment of the centrifugal pump-oxygenator, the magnetic impeller can be disposed on top of a motor drive base which incorporates preferably a rotatable magnet within, such that the rotatable magnet operatively engages and rotates the magnetic impeller positioned within the centrifugal pump.

It is a very surprising finding of the present invention that—besides the known advantages of pumping blood with a bearingless journalled rotor, namely providing a perfect sealing of the blood from the environment as well as a very gentle and careful pumping of the blood having very sensitive cell membranes—using such a magnetically journalled rotary drive in a centrifugal blood pump-oxygenator results in an extremely uniform blood flow through the fiber membranes, avoiding hyper- and hypo-perfusion of the blood in flow paths.

Using a rotary drive in an integrated centrifugal blood pump-oxygenator according to the present invention, the flow path through the fiber membranes can be significantly reduced in comparison to the oxygenators known from the state of the art, thereby reducing extended blood contact with the fiber membrane surfaces and, at the same time, not requiring the fiber membranes to have a large surface area. In particular the latter advantage of the present invention is very important in practice, since the larger surface area, as known from the oxygenators of the state of the art, and extended blood exposure time are the major contributing factors to the activation of blood-formed elements responsible for thrombosis, which risk is significantly reduced, or almost avoided, by using an oxygenator with a magnetic rotary drive in accordance with the present invention.

Another drawback of the state of the art, in particular regarding oxygenator systems in which the blood is passively pumped to flow through the fiber membranes, is that a relatively thick blood boundary layer of slow-moving blood is developed adjacent to the membranes. This phenomenon impedes the efficient exchange of gases from/to the blood cells. Therefore, gas membrane surface areas of 2 to 4 m$^2$, as already mentioned above, are typically required in the state of the art to provide the needed gas exchange. Consequently, the overall volume of the devices is impractical for portable deployment. In addition, the pumps used in the known ECMO systems or proposed by the above-cited state of the art patents all suffer device-induced blood trauma (hemolysis, and blood element activation) due to the technologies utilized (mechanical bearings, non-optimized flow paths, large prime volume, and so on).

All these drawbacks have been overcome for the first time by the present invention, by using a rotational body magnetically journalled in a contact-free manner with respect to a rotor-housing in combination with optimized flow paths of the blood through the oxygenator membrane.

Thus, the integrated centrifugal blood pump-oxygenator according to the present invention is a very compact, efficient and non-traumatic pump-oxygenator with pumping function, low prime volume and low gas exchange membrane surface area, providing an integrated magnetically levitated pump-oxygenator with a concept of controlled blood recirculation, resulting in a significant reduction of membrane surface which is preferably smaller than 1.0 m$^2$ and priming volume, and non-traumatic benefit compared with known current oxygenator technologies.

In a preferred embodiment in accordance with the present invention, the gas inlet enters the interior of the housing through the top of the housing and/or through a sidewall of the housing and/or the gas outlet exits the housing preferably through the bottom and/or through the sidewall of the housing and/or comprises a drain for blood or components thereof that enter a fiber of the oxygenator membrane, whereby the blood outlet may exit the housing through the top and/or through the sidewall of the housing.

In a special embodiment which is very important in practice, the blood inlet enters the interior of the housing essentially through a center of the top of the housing and/or the blood inlet traverses the interior of the housing, and operably connects with a frustoconical manifold, through which, in the operating state, blood is drawn by the rotational body.

Preferably, the bottom includes a diffuser blade, in particular a peripherally located, outwardly radiating diffuser blade, and/or the rotational body is preferably an impeller comprising essentially centrally located, preferably outwardly radiating blades, wherein the impeller is preferably disposed with respect to the frustoconical manifold of the blood inlet in such a way that, in the operating state, upon rotation, the blood that passes through the frustoconical manifold is forced through the oxygenator membrane by the rotating and levitating impeller.

In a very advantageous embodiment, the oxygenator membrane surrounds the blood inlet, in particular in the form of a cylinder, wherein the oxygenator membrane preferably comprises fibers, and/or an upper potting, and/or a lower potting, wherein the upper potting and the lower potting hold the fibers in place, forming in particular a cylindrical fiber structure surrounding the blood inlet.

Regarding another special embodiment of the present invention, the integrated centrifugal blood pump-oxygenator may further comprise a blood outlet manifold, which is preferably disposed between the oxygenator membrane and the top of the housing and/or is operably connected with the blood outlet, and/or the blood outlet manifold transfers blood in the operating state from the oxygenator membrane to the blood outlet.

The integrated centrifugal blood pump-oxygenator may also include a gas inlet manifold, which is preferably disposed between the oxygenator membrane and the top of the housing and/or is operably connected with the gas inlet, and/or which gas inlet manifold collects oxygen in the operating state from the gas inlet for an oxygenation of the oxygenator membrane.

The blood pump-oxygenator in accordance with the present invention can also comprise a gas outlet manifold, which is preferably disposed between the oxygenator membrane and the bottom of the housing and/or is operably connected with the gas outlet, and/or which gas outlet manifold collects carbon dioxide in the operating state from the oxygenator membrane.

In a further special embodiment which is very important in practice, a recirculation loop and/or a blood recirculation port and/or a blood recirculation valve is provided, which is preferably located between the blood inlet and the blood outlet and/or connects the blood outlet manifold with the blood inlet.

The blood pump-oxygenator can further comprise a blood heat exchanger and/or a blood temperature probe and/or a temperature controller, which blood temperature probe and/or which temperature controller is operably connected to the blood heat exchanger for probing and/or controlling the blood temperature in the operating state.

In another special embodiment, a blood inlet sample port and/or a blood outlet sample port may be additionally provided, and/or a blood reservoir can be provided in the interior of the housing and/or a blood reservoir being affixed to an exterior of the housing is in operable contact with the blood inlet and/or with the blood outlet.

Preferably, a blood gas sensor is in operable communication with the blood inlet and/or a blood gas sensor is preferably in operable communication with the blood outlet.

The invention relates also to an extracorporeal life support system comprising an integrated centrifugal blood pump-oxygenator as described in the present application, and/or further comprises a pump/motor controller, and/or an inflow cannulae and/or an outflow cannulae for conveying blood from and/or to the body of a patient and/or a tubing, and/or a motor.

Preferably, the extracorporeal life support system in accordance with the present invention includes a blood flow probe being connected to the pump/motor controller and/or includes a compliance chamber which is preferably provided between a patient, to whom the extracorporeal life support system is attached, and the extracorporeal life support system.

Regarding a special embodiment which is very important in practice, a blood gas sensor and/or a gas supply regulator is provided, which is operably connected to the pump/motor controller, and/or a blood heat exchanger is positioned before the blood inlet of the blood pump-oxygenator.

The extracorporeal life support system of the present invention can further comprise a blood temperature probe and monitor and a temperature controller, which are operably connected to the blood heat exchanger.

The present invention relates in addition to a method of de-bubbling and priming an extracorporeal life support system as described, which method comprises interconnecting a tube between the blood inlet and the blood outlet and circulating a priming solution through the tube into the system, whereupon the system is de-bubbled and primed.

In the following, some additional special and alternative embodiments and operational features of the integrated blood pump-oxygenator and the extracorporeal life support system, respectively, according to the present invention are discussed in more detail.

In the operation state, the pump function of the extracorporeal life support system draws venous blood through a vascular cannula into the integrated blood pump-oxygenator. Blood is aspirated into the oxygenator and discharges to a rotating impeller that imparts energy to propel the blood through the oxygenator to be oxygenated and returned back to the patient through an additional cannula. With the cannulae and the pump-oxygenator, the blood can be managed to have a pressure head of up to 120 mmHg to overcome the afterload of the pulmonary circulation or systemic circulation.

The impeller is configured as a finned element that is magnetically levitated and rotated by means of an external motor. The spinning impeller, through design and housing configuration, can generate pressures ranging from about 100-600 mmHg and results in blood flow rates through the system of 0-10 liters/minute at impeller speed ranging from 0-5500 rpm. Impeller configuration is determined by both pressure-flow needs and the bearingless motor technology constraints, which may be tailored to desired performance. Utilizing the MagLev intellectual property, bearingless motor technology provides an effective means to pump blood with minimal blood trauma and reliability. The configuration of the impeller blades, length and number, recirculation lumen and flow path may be detailed to meet performance needs when coupled with the associated housing configuration. It is possible to adapt the pump portion of the pump-oxygenator device to the marketed CentriMag motor and electronic controller. Alternatively, the UltraMag motor and controller could be considered for smaller device sizes.

In the operation state, the blood flows through the diffuser fins in the periphery of the pump housing chamber on its way into the oxygenator housing. These diffuser fins convert the blood kinetic energy (rotational flow velocity) into pressure for improved flow dynamics through the rest of the device. The outlet of the diffuser volute feeds the fiber membrane manifold portion of the device.

The oxygenator portion of the device consists of a blood feed annulus which is contiguous with the pump discharge. This annulus feeds a circumferential cylinder-like manifold that distributes the blood 360° about a fiber bundle. The purpose of the fiber as a membrane of the oxygenator is to maintain a separation of the blood and gas phases (as compared to that of a bubble oxygenator where oxygen is bubbled directly into the blood reservoir). Maintaining separation is much safer since gaseous emboli (if the gas pressures are maintained below that of the blood pressure) are not formed in the blood. The fiber bundle is composed of thousands of microporous fibers with sizes less than 0.1 micron. Alternatively, coated or skinned fibers may be utilized which permit oxygen and carbon dioxide diffusion through a non-porous skin layer of the outer wall of the fibers. The fibers are typically available commercially in a tape configuration whereby individual fibers are arranged to a predetermined configuration (i.e. parallel straight or bias, multi-directional, woven, spaced, etc.) permitting tape wrapping to form a cylindrical or conical-like bundle configuration. Alternatively, the fiber can be wrapped or wound like a spool of kite string. The ends of the fiber bundle are cast potted in, for example, a polymer (like urethane) and the bundle ends with potting are trimmed to open the internal passages of the hollow fibers. It is through these inner lumens that the sweep gas is distributed. The blood and gas are structurally separated. The membrane fibers are commercially available and range in size from 250 to 400 micron outside diameter with a wall thickness of approximately 30 to 50 microns.

The fiber bundle may or may not include an anti-thrombogenic coating containing heparin or functional equivalent attached to the outside of each fiber.

Unique to this device according to the present invention, the blood supply is fed through a 360° annulus manifold about the pump discharge from the outer wall of the fiber bundle. This provides equal pressure distribution through the circumferential manifold about the bundle. Contained within the oxygenator housing is a membrane fiber bundle. With the residual circumferential velocity of the blood after the pump diffuser, the blood distributes inward radially through the fiber bundle over the outer surface of the individual fibers resulting in radial and circumferential flow dynamics. Low pressure radial flow through the bundle results in adequate blood creating blood mixing to continuously reduce the boundary layer of the blood and place red blood cells in closer contact to alleviate $CO_2$ and diffuse $O_2$. The blood is collected in a manifold at the core of the device and is driven to the pump outflow.

The flow dynamics in the device have been optimized to reduce zones of stagnation that could result in blood stasis and the potential for clotting. Stagnant areas are low- or no-flow areas which occupy critical membrane surface area, effectively reducing the performance of the design.

The oxygenated "arterial" blood collected in the center core manifold is co-axial to the inflow "venous" blood. To collect the flowing blood, an outlet manifold is constructed with consideration to flow dynamics to connect to the blood outlet fitting (that connects to the outflow cannula for patient blood return). The unique co-axial design allows that the inflow and outflow cannulae can be arranged closely in parallel, which is desirable in a clinical setting. The device inflow and outflow connectors can be sized as required for desired blood rates and pressures. Typically, such devices are fitted with ¼" or ⅜" barbed fittings receiving standard extracorporeal tubing.

At either end of the fiber bundle is a gas inlet and outlet manifold. The inlet manifold distributes oxygen gas to the open lumen fibers imbedded in potting material. Transversing the fiber length at a controlled flow velocity, the oxygen flow will alleviate the carbon dioxide from the blood and make available oxygen for diffusion into the blood. The inlet gas pressure must be less than the blood pressure produced on the outside of the membrane fiber to assure the user that broken fibers will result in blood leaking into the gas phase rather than gas bubbles emerging into the blood. The membrane fibers must be configured such that they are the same effective length from inlet to outlet to maximize gas transfer efficiency and maintain a uniform gas flow through all fibers simultaneously. As the membrane bundle is essentially suspended within the structure of the device, the gas outlet is conducted through channels (in this case, tubes) contained within the diffusers to exhaust.

The gas outlet manifold collects the gas and permits venting, typically to the atmosphere. In addition, the outlet gas manifold contains a means to drain plasma or whole blood should it enter the membrane fibers. This is particularly important for longer run ECMO cases where lipids in the blood wet the porous structures in the fibers and eventually result in plasma leakage. This condition could occur with sealed fibers should they become damaged and crack.

Another optional design feature that may be incorporated with or integrated into the pump-oxygenator according to the invention is a blood recirculation port/valve. This port will shunt the oxygenated, patient-return blood back to the pump inflow line to enable a portion of the blood to re-flow through the oxygenator bundle to increase oxygen concentration. Such recirculation could reduce the amount of membrane surface area of the oxygenator and subsequent priming volume of the device. The recirculation valve/port should be positioned between the venous blood and arterial blood of the device and can be placed at various positions between the two conditions. One proposed design incorporates the ability to adjust the flow rate through the shunt. This may be a critical feature when dealing with neonatal patients where blood volume of the patient is extremely small.

The recirculation loop is also useful during device set-up and priming by enabling saline to effectively circulate through the device (with the inflow and outflow ports capped), eliminating any harmful air bubbles that may be trapped between the bundle fibers and pump housing.

The device may contain arterial and venous sample ports permitting blood samples to be collected by syringe, such as traditional stopcocks or obturator-type sample ports. The sampling ports must enable whole blood extracted from sites before and after the oxygenator bundle to enable the user to adjust blood flow rates, gas transfer rates and pH for control of oxygen concentration.

The device must be positioned such that a vent port is positioned at the portion of the device where air bubbles will accumulate. It is important to be able to remove gaseous bubbles from the device during use. Bubbles typically result from trapped air not adequately de-bubbled during priming, broken membrane fibers or excessive negative pressure applied to the blood drawing gas out of solution.

Accessories to the Pump-Oxygenator System may include for example:

Ultrasonic Flow Probe—This device measures blood flow as it flows through the tubing out from and/or in to the device. Current technology (Transonic Flow Probe—PXL series) enables a box-like sensor to be placed about the tubing and assesses the blood non-invasively. This device (or equivalent) is electronically integrated into the CentriMag Electronic Controller providing feedback for blood flow control.

Temperature Probe—This device measures blood temperature returning to the patient and alerts the user if excessive heat loss occurs. When combined with a blood heat exchanger device, normothermic blood temperature may be maintained should excessive heat loss occur.

Blood Heat Exchanger—This is typically a water-based shell and tube-type heat exchanger that controls the blood temperature as it circulates in or about the heat exchanger core. Although improvements in technology can provide over-temperature protection from over-heating the blood (above 42° C.), water (or other medium) provides another level of safety over direct temperature control. As such, a heat exchanger controller maintains set temperature from a larger mass of water built into the controller device. A blood heat exchanger device may be integrated in the pump-oxygenator or a separate device, positioned before the oxygenator bundle (preferred). Such a device may be positioned before the blood inflow of the pump-oxygenator. Regardless of the design configuration, the water and blood phases must be structurally separated.

Compliance Chamber—This is typically utilized when there are expected changes in the vasculature. Medically induced vasoconstrictors can dramatically affect blood pressure. A compliant chamber placed in series to the patient can absorb the extra volume resulting from constriction of a closed system. More typically, in ECMO utilization, the patient is effectively their own reservoir and a compliance chamber may not be required.

Blood Reservoir—This is a holding chamber for excess blood. This device is critical for open heart surgery or trauma where blood losses, large blood temperature swings and medicines require extra volume storage. The pump-oxygenator may be adapted to contain or affix a blood reservoir, but for ECMO utilization a reservoir is not required.

Blood-Gas Sensors—These are devices utilized to assess real-time blood gases ($O_2$ and $CO_2$). Special connectors are required of Blood-Gas manufacturers and they may be integrated into the device for sensor connection or placed in-line on the tubing set connected to the pump-oxygenator device.

Prime Circuit—This is a sterile tube pack that enables the user to rapidly set up and prime the by-pass circuit, interconnecting the saline priming solution bags/containers to the pump-oxygenator device. This circuit is connected to the inflow connector and outflow connector and permits fluid circulation to de-bubble and prime the extracorporeal circuit.

Alternative embodiments may address the designs, applications, materials, coatings, uses, accessories, construction processes, costs, etc.

Current Extracorporeal Life Support (ECLS) systems are generally too large to allow patient mobility, are attached via large-bore cannulae inserted from the neck and groin, require full systemic anti-coagulation with heparin, and generally utilize porous hollow fiber oxygenators that need to be replaced every few days. The design proposed by the present invention (pump, oxygenator, motor, controller, etc.) is scaleable (larger or smaller). With considerations for cannulae placement into the patient (e.g. pump-lung system placed between the right atrium (RA) and pulmonary artery (PA)) to maintain physiological requirements, the system can be portable and wearable and can be employed in all patients with or without accompanying elevated pulmonary vascular resistance. As such, the technology development is scaleable to be portable and eventually wearable. Such a device would enable today's bedridden patient to be ambulatory.

Alternative design configuration for oxygen supply in the device may include photolytic blood oxygenation as described in U.S. Pat. No. 6,866,755. Such a design would replace the hollow fiber membrane and oxygen supply and be substituted with coated optical diffusion conduits or fibers for blood contact activated with ultraviolet light. The blood side of the device would be similar to the membrane oxygenator described above and incorporate an integrated blood pump.

Another design alternative could substitute the oxygenator fiber with hollow fibers enabling a heat exchanger. Such a configuration would also utilize hollow tubes, the insides of which could flow temperature-controlled water to effect blood temperature change/maintenance.

Another design alternative could include microporous membranes to filter blood components as utilized in blood dialysis.

Another design alternative could include a filter means (depth filter, reticulated foam, microporous filtration, filtration mediums, etc.) to capture particulate as a fluid is driven through the filter.

Furthermore, the invention relates to a method of reducing hyper- and hypo-perfusion of blood comprising the following steps: providing an integrated centrifugal blood pump-oxygenator comprising a housing with a top having a blood inlet, a blood outlet and a gas inlet, and a bottom having a rotational body being rotatably arranged in a rotor-housing of the bottom, as well as an oxygenator membrane provided in an interior of the housing; transferring oxygen from the gas inlet through the oxygenator membrane to an gas outlet; and bringing blood in direct contact with the oxygenator membrane by pumping the blood by the rotational body from the blood inlet to the blood outlet, wherein the rotational body is magnetically journalled in a contact-free manner with respect to the rotor-housing.

In addition, the invention relates to a method of reducing hyper- and hypo-perfusion of blood comprising the following steps: providing an extracorporeal life support system comprising an integrated centrifugal blood pump-oxygenator in accordance with the present invention, and/or further comprising a pump/motor controller, and/or an inflow cannulae and/or an outflow cannulae and/or a tubing, and/or a motor.

BRIEF DESCRIPTION OF THE DRAWINGS

In the following, the invention will be explained in more detail with reference to the drawings.

FIG. 2b illustrates crossed biased fibers according to FIG. 2a;

DESCRIPTION OF THE PREFERRED EMBODIMENTS

Figure 1:
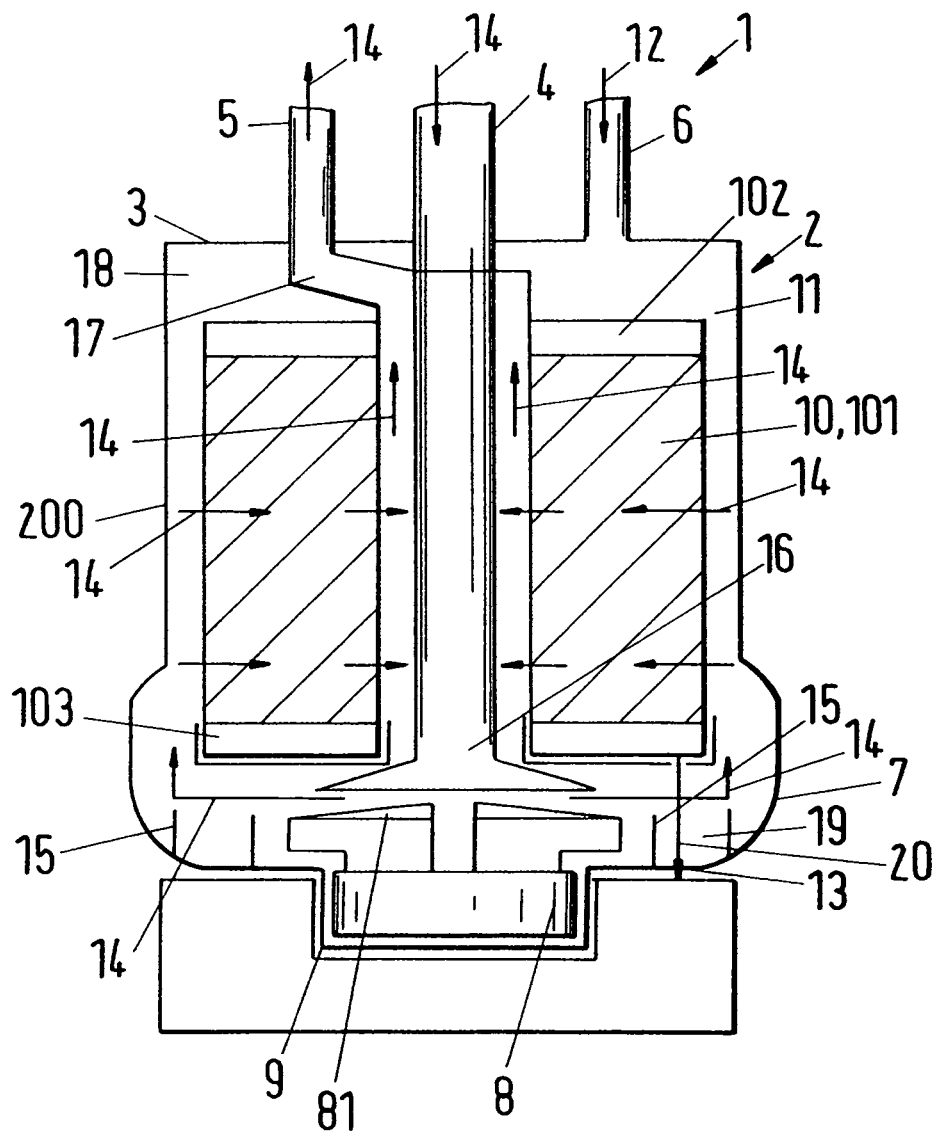
FIG. 1 is a longitudinal cross-sectional view of an integrated blood pump-oxygenator of the present invention.

The present invention provides an integrated centrifugal blood pump-oxygenator, an extracorporeal life support system, and a method of de-bubbling and priming the extracorporeal life support system. Blood is simultaneously drawn from and returned to the patient. The blood pump-oxygenator controls blood recirculation, thereby enabling significant reductions in membrane surface area (i.e. $<1.0$ $m^2$) and priming volume in comparison to currently available oxygenator technologies. Effective blood pumping is achieved, while minimizing blood trauma, through the use of a bearingless, magnetically levitating and rotating impeller. The blood pump-oxygenator can maintain adult and pediatric pumping and respiratory functions for 14 days or more.

Various forms of extracorporeal life support (ECLS) have recently emerged. Veno-arterial ECLS provides complete $O_2$ and $CO_2$ exchange and has been shown to improve survival in neonatal and selected adult patients.

The pump-oxygenator according to the present invention includes the magnetically levitated bearingless pump and motor technology and uniquely configured hollow fiber membranes to provide a low prime, low hemolytic blood pump-oxygenator capable of providing respiratory support or ECMO support for pediatric and adult patients.

The system incorporates an integrated pump-oxygenator that simultaneously draws blood from the patient's vasculature through percutaneous or surgically implanted cannula, induces pressure to the blood flow through a rotating centrifugal pump impeller, drives the blood through a gas-permeable hollow fiber membrane bundle to effect carbon dioxide removal from the blood and supply oxygenation to the blood, and returns the oxygenated blood to the patient's vasculature through another cannula or conduit.

The oxygenator membrane portion removes $CO_2$ from the blood and adds $O_2$ to increase oxyhemoglobin concentration in the blood. A number of factors largely affect this condition: blood pH, blood flow rate, $O_2$ gas sweep rate, blood temperature, blood hematocrit, blood cell-plasma boundary layer thickness at the surface of the membrane fiber, preferential flow conditions by design or from clot formation, and blood damage induced by shear.

The size of the fiber bundle can vary depending on need/application. For adult ECMO utilization, gas transfer rates between 200 ml/minute and 400 ml/minute can be expected at blood flow rates between 2 liters/minute and 7 liters/minute. The efficiency of the blood flow dynamics, gas transfer efficiency, percent membrane porosity or permeability rate, fiber size, etc. has an effect on gas transfer efficiency. Exposed membrane surface area can range from 0.5 to 2.5 $m^2$. According to the present invention, blood contact membrane surface areas of $<1.0$ $m^2$ are possible. Pediatric ECMO will utilize a lower flow rate range and reduced surface area membrane.

Alternative uses like those encountered during cardiac bypass surgery may require more reserve gas transfer, which relates to increased surface area. Such oxygenators known from the state of the art require gas transfer support of patients whose core body temperature is reduced to 28° C. and re-warmed rapidly upon completion of the cardiac procedure. It is not uncommon to utilize oxygenators with surface areas>3 $m^2$. The more foreign material and flow-induced shear exposed to the blood, the greater the incidence of blood trauma and blood reactions.

The integrated centrifugal blood pump-oxygenator in accordance with the present invention, which is overall in the following designated by the reference numeral 1, comprises in the special embodiment shown in FIG. 1 a housing 2, a blood inlet 4, a frustoconical manifold 16, a bearingless magnetically levitating and rotating rotational body 8 which is according to FIG. 1 an impeller 8, an oxygenator membrane 10 being placed between an upper potting 102 and a lower potting 103, a blood outlet manifold 17, a blood outlet 5, a gas inlet manifold 18, a gas inlet 6, a gas outlet manifold 18, a gas outlet 13, and a vent port.

The housing 2 comprises a top 3, a bottom 7 with peripherally located, outwardly radiating diffuser blades 15 and gas outlet(s) 13, a sidewall 200, an interior 11, and an exterior outside of the housing 2. The sidewall 200 preferably is of cylindrical shape. The housing 2 can be manufactured from any suitable material in accordance with methods known in the art. For example, the housing 2 can be made from plastic materials, in particular an injection moldable plastic, such as polycarbonate, ABS, thermoplastic polyurethane or any other suitable material. Preferably, the housing 2 is sterilizable by a chemical sterilant, such as ethylene oxide, radiation, or other sterilization method, or is a single-use housing 2.

The blood inlet 4 enters the interior 11 of the housing 2 through the center of the top 3 of the housing 2, traverses the interior 11 of the housing 2, and operably connects with the frustoconical manifold 16. In the operation state, venous blood 14 is drawn through the blood inlet 4.

The blood outlet manifold 17 is disposed above the oxygenator membrane 10 and below the top 3 of the housing 2. The blood outlet manifold 17 transfers blood 14 from the oxygenator membrane 10 to the blood outlet 5.

The blood outlet 5 is operably connected with the blood outlet manifold 17 and exits the housing 2 through the top 3 or the sidewall 200. Preferably, the blood outlet 5 exits the housing 2 as shown in FIG. 1 through the top 3.

The gas inlet manifold 18 is disposed above the oxygenator membrane 10 and below the top 3 of the housing 2. The gas inlet manifold 18 collects oxygen 12 from the gas inlet 6 for oxygenation of the oxygenator membrane 10.

The gas inlet 6 enters the interior 11 of the housing 2 through the top 3 of the housing 2 or the sidewall 200 of the housing 2 and operably connects with the gas inlet manifold 18. Preferably, the gas inlet 6 enters the interior 11 of the housing 2 through the top 3.

The gas outlet manifold 19 is disposed below the oxygenator membrane 10 and above the bottom 7 of the housing 2. The gas outlet manifold 19 collects carbon dioxide 20 from the oxygenator membrane 10.

The gas outlet 13 exits the housing 2 through the bottom 7 or the sidewall 200, operably connects with the gas outlet manifold 19, and comprises a drain for blood 14 or components thereof that enter the fibers 101 of the oxygenator membrane 10. Preferably, the gas outlet 13 exits the housing 2 through the bottom 7.

The flow paths of blood 14 and oxygenation gases 12 are demonstrated in FIG. 1 by arrows 14 and 12, respectively.

The bearingless, magnetically levitating and rotating impeller 8 is disposed beneath the frustoconical manifold 16 of the blood inlet 4 and above the bottom 7 of the housing 2.

The impeller 8 comprises centrally located, outwardly radiating blades 81. Upon rotation of the centrally located, outwardly radiating blades 81, the impeller 8 forces blood 14, which has passed through the frustoconical manifold 16, through the oxygenator membrane 10.

The oxygenator membrane 10 comprises fibers 101, upper potting 102, and lower potting 103. Any suitable potting material having good adhesion properties can be used for the upper potting 102 and the lower potting 103. Examples of suitable potting materials include, but are not limited to, polyurethane resin.

Figure 2A:
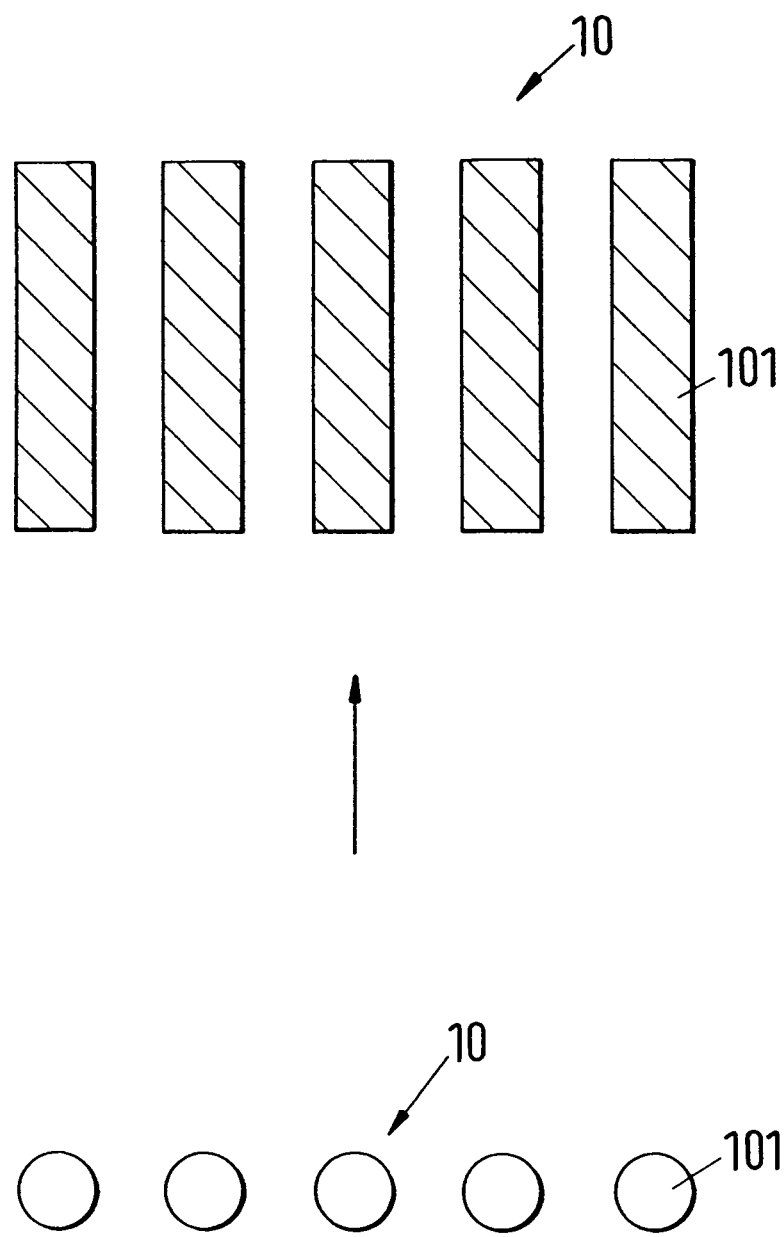
FIG. 2a illustrates parallel fibers for use in the oxygenator membrane of an integrated blood pump-oxygenator in accordance with the present invention.
Figure 2B:
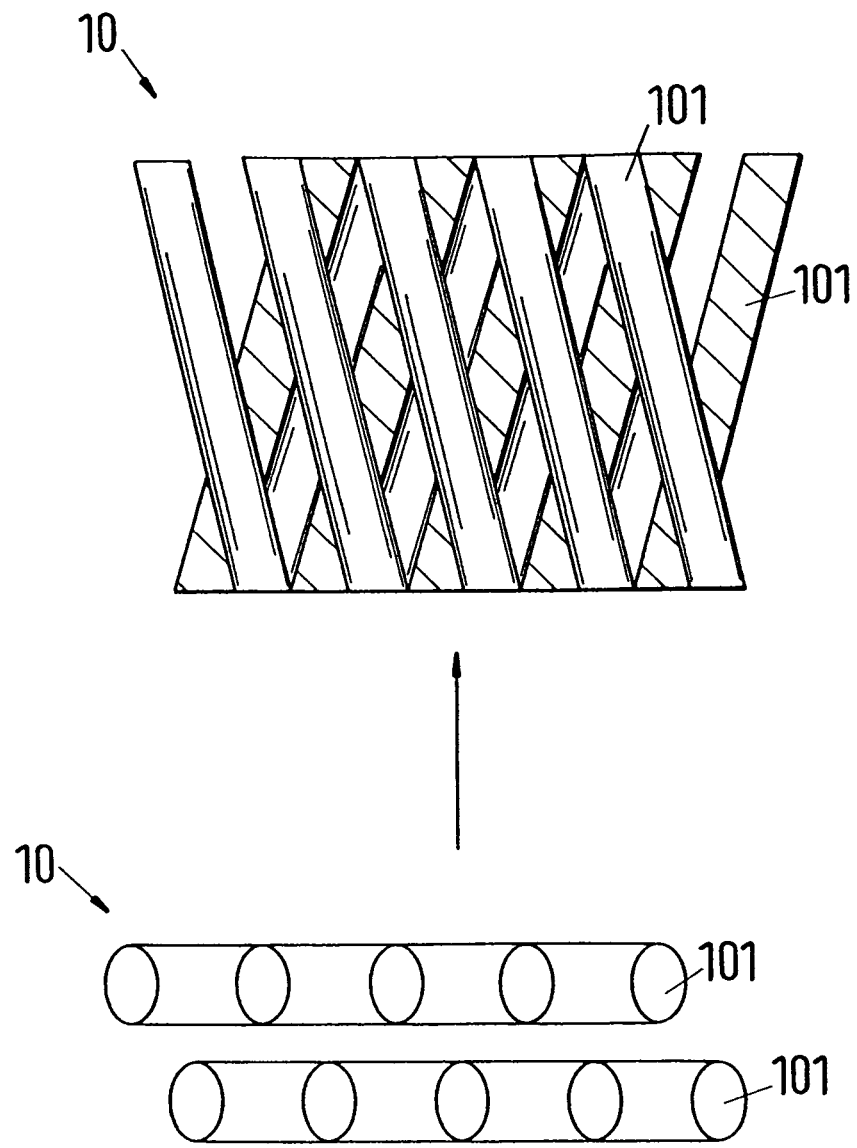

In the operating state, the fibers 101, which are shown in more detail in FIG. 2a and FIG. 2b, oxygenate the blood 14. Any suitable fibers 101 can be used to oxygenate the blood 14. Examples of suitable fibers 101 include, but are not limited to, microporous hollow fibers 101 of cellulosics, polyolefins, polysulfones, polyvinyl alcohol, silicone resins, poly(methyl methacrylate), and the like (e.g. Celgard® microporous polypropylene fibers, which are available from Membrana, Charlotte, N.C., or Polypropylene Hollow Fiber KPF or Polyethylene Hollow Fiber EHF, which are available from Mitsubishi Rayon Co., Ltd., Tokyo, Japan) or sealed fibers 101.

If the fibers 101 are hollow, the fiber lumens communicate with the outer surfaces of the upper potting 102 and the lower potting 103 so that, when oxygenating gas 12 is introduced via the gas inlet 6, the gas 12 flows into the gas inlet manifold 18, then into the open ends of the hollow fibers 101 at the outer surface of the upper potting 102, through the lumens of the hollow fibers 101, through the open ends of the hollow fibers 101 at the outer surface of the lower potting 103, and out the gas outlet 13.

If the fibers 101 are sealed, oxygen and carbon dioxide diffuse through a non-porous skin layer on the outer surfaces of the fibers 101.

According to FIG. 2a and FIG. 2b, the fibers 101 can be parallel, straight, on a bias, multi-directional, woven, spaced, configured as a tape, and the like. Fibers 101, which are already configured, can be obtained from a commercial supplier. Alternatively, the fibers 101 can be wound with a winding apparatus, such as the Precision Wind Take-Up Machine (Leesona Corp, Burlington, N.C.) or an equivalent thereof.

FIG. 2a and FIG. 2b, respectively, exemplify parallel fibers 101 and crossed biased fibers 101 for use in the oxygenator membrane 10. The fibers should be packed at a density that avoids blood 14 channeling and hemolysis. The fibers 101 exhibit a degree of packing (the proportion of the total cross-sectional area of the hollow fibers 101 to the total cross-sectional area of the oxygenator membrane 10 in a plane parallel to the direction of blood flow) of about 10-55%, preferably of about 15-45%, more preferably of about 20-40%.

The fibers 101 can be coated with an anti-thrombogenic agent, such as heparin or a functional equivalent thereto. As shown in FIG. 1, the upper potting 102 and lower potting 103 hold the fibers 101 in place.

Figure 3:
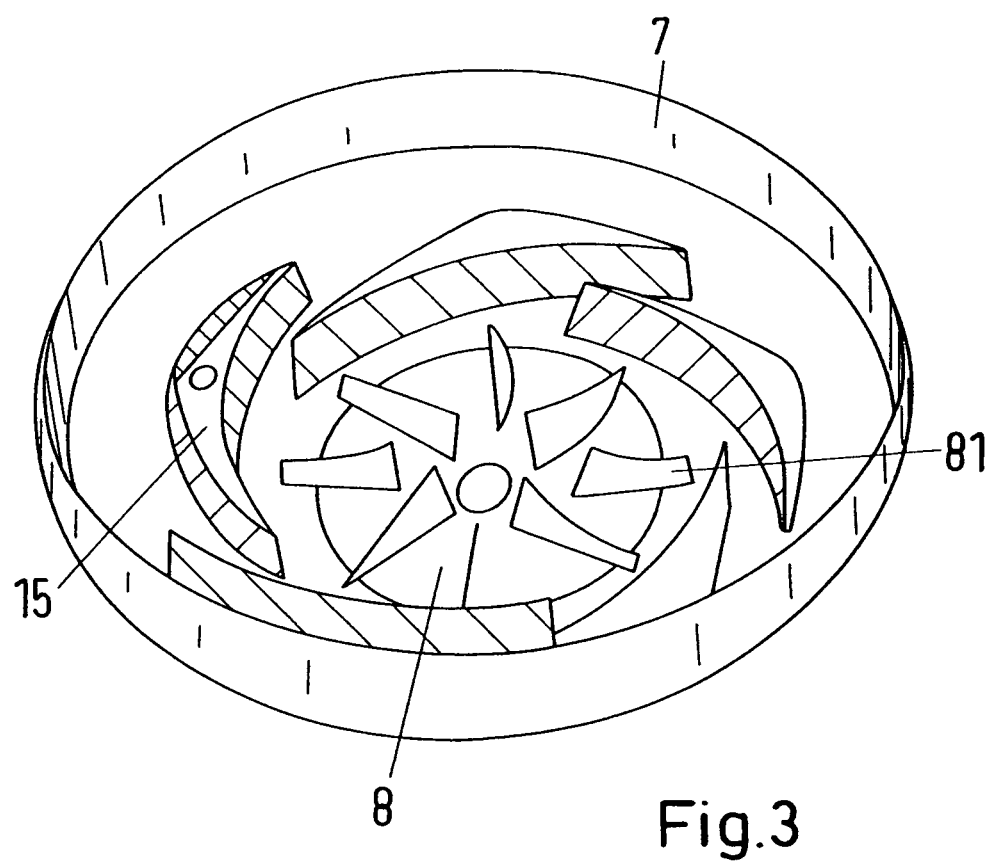
FIG. 3 is an internal top view of the rotational body and the bottom of an integrated blood pump-oxygenator in accordance with the present invention.

In FIG. 3, the rotational body 8 and the bottom 7 of an integrated blood pump-oxygenator 1 in accordance with the present invention are schematically shown by an internal top view in more detail. As already mentioned, the bearingless, magnetically levitating and rotating impeller 8 shown in FIG. 3 is disposed beneath the frustoconical manifold 16 of the blood inlet 4 and above the bottom 7 of the housing 2, as schematically shown in FIG. 1. The impeller 8 comprises centrally located, outwardly radiating blades 81. Upon rotation of the centrally located, outwardly radiating blades 81, the impeller 8 forces blood 14, which has passed through the frustoconical manifold 16, through the oxygenator membrane 10.

Figure 4:
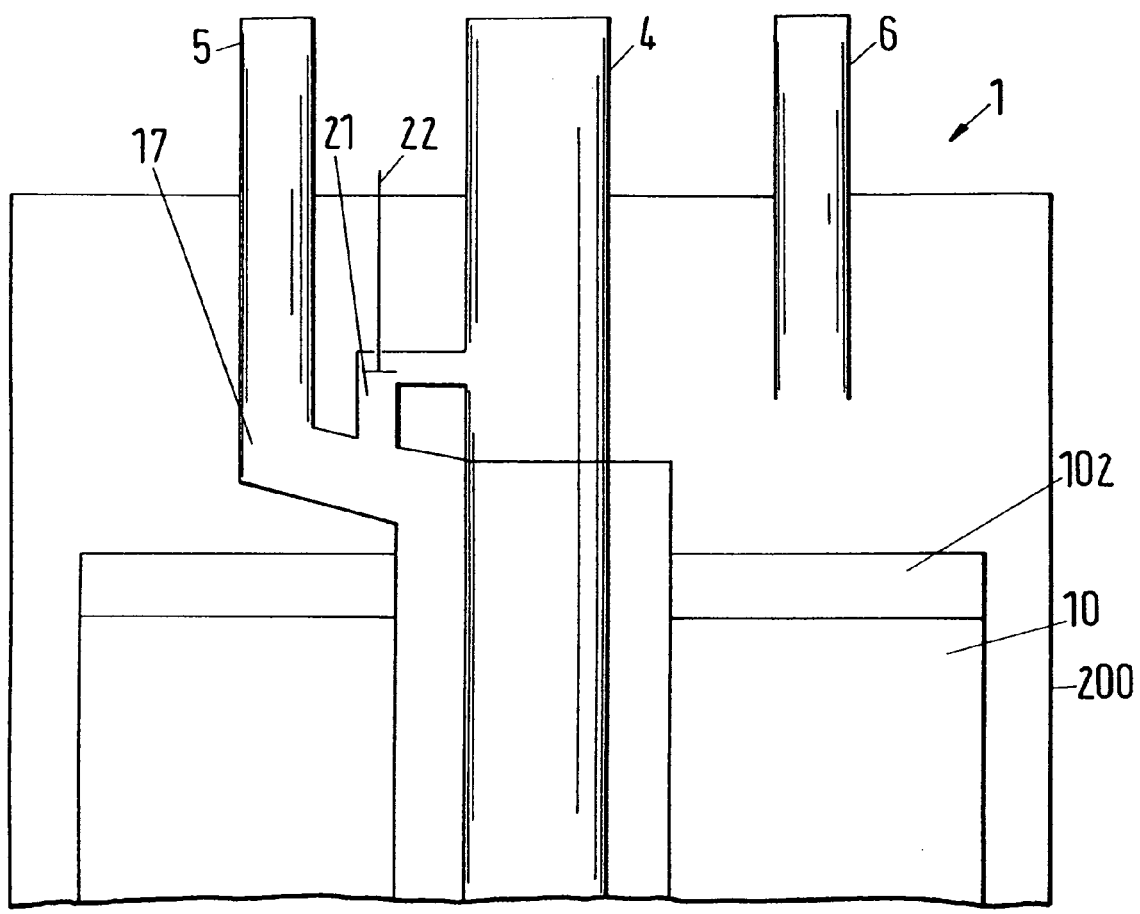
FIG. 4 is a longitudinal cross-sectional view of an example of a recirculation loop in an integrated blood pump-oxygenator of the present invention.

FIG. 4 is a longitudinal cross-sectional view of an example of a recirculation loop 21 in an integrated blood pump-oxygenator 1 according to the present invention, comprising the blood outlet 5, the blood inlet 4, the gas inlet 6, all being placed at the top 3 of the housing 2. Also shown in FIG. 4 is the sidewall 200 of the housing 2, and the recirculation loop 21. The blood recirculation loop 21 which is in FIG. 4 a blood recirculation port 21 includes a valve 22 and can be situated in any suitable position relative to the blood inlet 4 and the blood outlet 5. Preferably, the blood recirculation port 21 and/or the valve 22 can be located between the blood inlet 4 and the blood outlet 5 and connect the blood outlet manifold 17 with the blood inlet 4.

If desired, the integrated centrifugal blood pump-oxygenator can further comprise a blood inlet sample port and a blood outlet sample port. Any suitable port can be used. For example, the ports can be traditional stopcocks or obturator-type sample ports.

Regarding further special embodiments, which are not shown or not shown in greater detail in the drawings, the integrated centrifugal blood pump-oxygenator 1 can further comprise a blood heat exchanger. Alternatively and preferably, the heat exchanger can be maintained separately and positioned before oxygenator membrane 10, such as before the blood inlet 4, i.e. upstream of the blood inlet 4. Any suitable blood heat exchanger can be used as long as the coolant (e.g. water) and blood phases are structurally separated. For example, a water-based shell in combination with a tube-type heat exchanger that controls the temperature of the blood as it circulates in or about the heat exchanger core can be used. Although metallic tubules having good thermal conductivity can be used as the tubules for heat exchange, it can be preferable to use non-porous hollow fibers of plastic material, such as polyethylene or polypropylene, having an internal diameter of about 5-1,000µ and a wall thickness of about 2-20µ. Porous hollow fibers also can be used, provided the pores do not extend from one surface to the other surface.

If a blood heat exchanger is used, the blood pump-oxygenator 1 can further comprise a blood temperature probe and a temperature controller, which are operably connected to the blood heat exchanger. In the operating state, the temperature probe measures the temperature of the blood 14 as it returns to the patient and alerts the user if excessive heat loss is occurring. Normothermic blood temperature then can be maintained with the blood heat exchanger.

The blood reservoir can be placed in the interior 11 of the housing 2 or affixed to the exterior of the housing 2 in operable communication with the blood outlet 5. Any suitable reservoir can be used. The reservoir should be large enough to accommodate excess blood loss, such as that which occurs during open heart surgery or trauma, when there are large swings in blood temperature, or the medicines used necessitate a larger storage volume. The reservoir can incorporate one or more blood filtering elements as well as one or more blood defoaming elements.

A blood gas sensor in operable communication with the blood inlet 4, and an additional blood gas sensor in operable communication with the blood outlet 5, also can be included. The sensors assess blood gases (e.g. $O_2$ and $CO_2$) in real-time. Special connectors are required and can be obtained from suppliers for integration into the blood pump-oxygenator or for placement in-line on the tubing.

In view of the above, the present invention further provides an extracorporeal life support (ECLS) system 1000 comprising the integrated centrifugal blood pump-oxygenator 1, a pump/motor controller 1001, inflow and outflow cannulae for conveying blood from and to the patient, tubing, and a motor.

Figure 5:
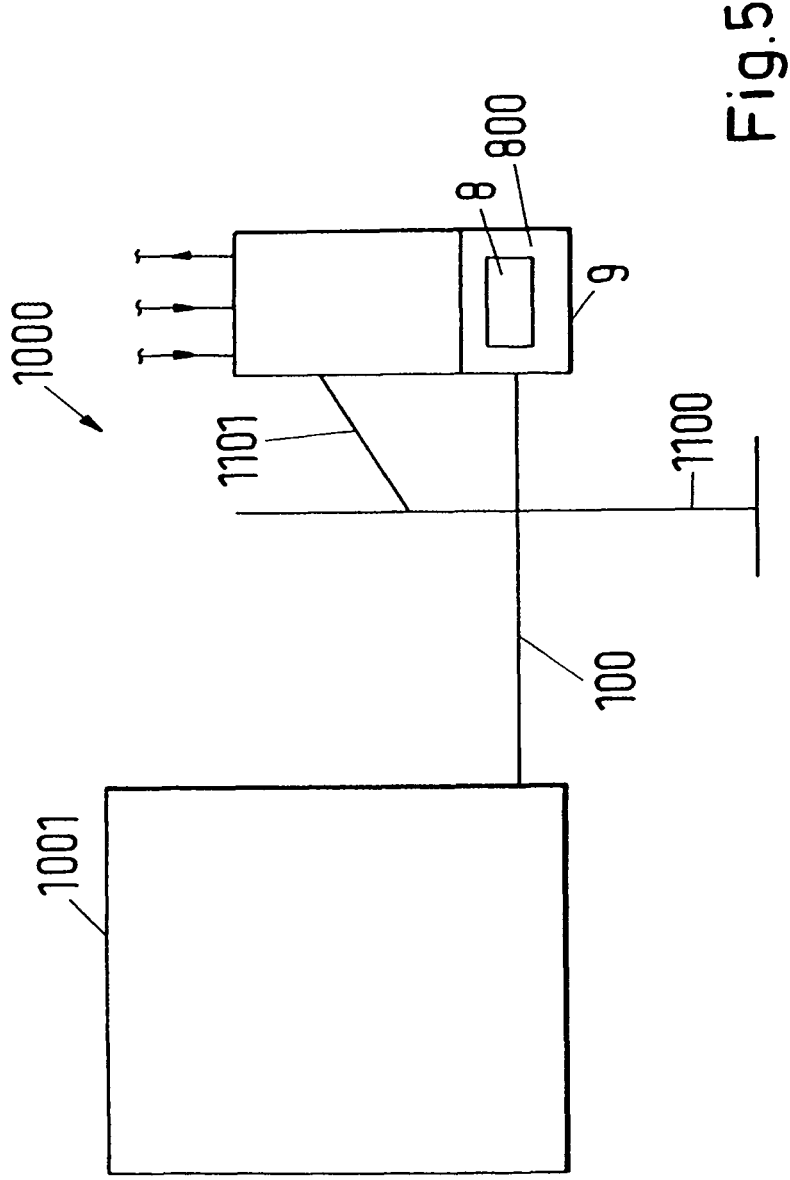
FIG. 5 is a schematic view of an extracorporeal life support system in accordance with the present invention.

A simple schematic example of an extracorporeal life support system 1000 is shown in FIG. 5, including the integrated blood pump-oxygenator 1 as described above, the motor 800 comprising the magnetically journalled rotational body 8 in the rotor-housing 9, a support stand 1100, a stand clamp 1101, and the pump/motor controller 1001.

Any suitable motor 800 can be used. The motor drive can be made of metal, plastic, or any other material, and generally does not need to be subjected to sterilization. The centrifugal pump-oxygenator 1 with the magnetic impeller 8 is disposed on top of a motor drive base which preferably includes a rotatable magnet within, such that the rotatable magnet operatively engages and rotates the magnetic impeller positioned within the centrifugal pump.

It is understood that in another embodiment the motor 800 may be provided by a stator including a drive winding with a strand for generating a magnetic drive field which produces a torque on the rotor 8, as above described in more detail.

Like the motor 800, any suitable controller 1001 can be used. The controller 1001 generally enables control of various operational variables, such as pump speed, motor speed, blood flow rate, and arterial pressure. For example, the CentriMag® motor 800 and electronic controller (Levitronix) 1001 can be used. Especially, the UltraMag® motor 800 and the electronic controller (Levitronix) 1001 can be used for small devices.

Figure 6:
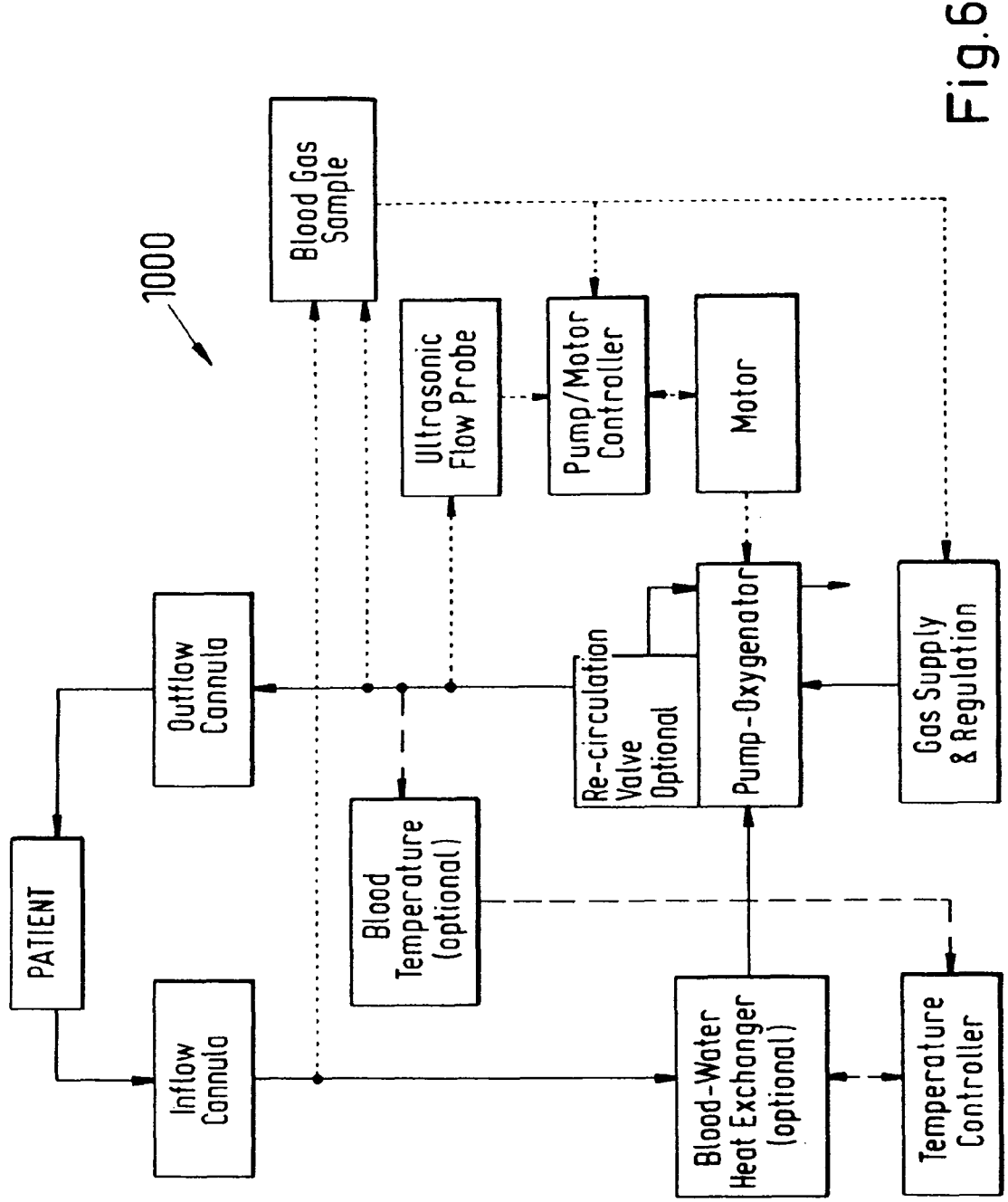
FIG. 6 is a diagram of an example of a blood pump-oxygenator control system in accordance with the present invention.

FIG. 6 is an example of a diagram of a blood pump-oxygenator control system for controlling an extracorporeal life support system 1000 in accordance with the present invention. Any suitable inflow and outflow cannulae and tubing can be used as are known in the art.

The extracorporeal life support system 1000 (ECLS) preferably is sized and configured to be positionable beneath or adjacent to a patient treatment table or operating table. The pump-oxygenator and the motor can be attached to a vertical pole or other support as shown in FIG. 5.

The extracorporeal life support system 1000 can comprise a blood flow probe, such as an ultrasonic flow probe, connected to the pump/motor controller. The flow probe measures blood flow as it flows through the tubing out from or in to the device. Any suitable ultrasonic flow probe can used as in the art. For example, a box-like sensor, such as the Transonic Flow Probe (such as those commercially available from Harvard Apparatus, Holliston, Mass.), can be placed about the tubing to assess blood flow non-invasively. The flow probe can be electronically integrated into the pump/motor controller to provide feedback for blood flow control.

The extracorporeal life support system 1000 can comprise a compliance chamber (not shown in FIG. 6) between a patient, to whom the extracorporeal life support system 1000 is attached, and the extracorporeal life support system 1000. A compliance chamber is typically used when there is an expected change in the vasculature, such as when a vasoconstrictor is used. A compliance chamber placed in series with the patient can absorb the extra volume resulting from constriction of the vasculature.

If not integrated into the blood pump-oxygenator 1, a blood gas sensor can be placed in-line on the tubing and a gas supply regulator can be operably connected to the pump/motor controller 1001.

If not integrated into the blood pump-oxygenator 1, a blood heat exchanger can be positioned before the blood inlet 4. A blood temperature probe and a temperature controller then can be operably connected to the blood heat exchanger.

An extracorporeal life support system 1000 comprising the integrated centrifugal blood pump-oxygenator 1 as described above and comprising a blood gas sensor in operable communication with the blood inlet 4 and another blood gas sensor in operable communication with the blood outlet 5, a pump/motor controller 1001, inflow and outflow cannulae and tubing, a motor 800, and a gas supply regulator, which is operably connected to the pump/motor controller 1001, is also provided.

As already mentioned, according to the present invention, a method of de-bubbling and priming an above-described extracorporeal life support system 1000 is also provided. The method comprises interconnecting a tube between the blood inlet 4 and the blood outlet 5 and circulating a priming solution through the tube into the extracorporeal life support system 1000.

The blood pump-oxygenator 1 is preferably scaleable. The extracorporeal life support system 1000 can be portable and wearable and can be employed in all patients with or without accompanying elevated pulmonary vascular resistance. Such a device would enable a bedridden patient to be ambulatory. If implanted, the housing is desirably made from a biologically compatible material, such as titanium.

Summarizing the present invention, for the first time an integrated centrifugal blood pump-oxygenator is provided, including a housing, which comprises a top, a bottom with peripherally located, outwardly radiating diffuser blades, a sidewall, an interior, and an exterior, a blood inlet, which enters the interior of the housing through the center of top of the housing, traverses the interior of the housing, and operably connects with a frustoconical manifold, and through which venous blood is drawn, a frustoconical manifold, a bearingless magnetically levitating and rotating impeller, which is disposed beneath the frustoconical manifold of the blood inlet and above the bottom of the housing and which comprises centrally located, outwardly radiating blades, which, upon rotation, force blood that passes through the frustoconical manifold through an oxygenator membrane, an oxygenator membrane, which surrounds the blood inlet and which comprises fibers, an upper potting, and a lower potting, wherein the upper potting and lower potting hold the fibers in place, a blood outlet manifold, which is disposed above the oxygenator membrane and below the top of the housing and transfers blood from the oxygenator membrane to a blood outlet, a blood outlet, which is operably connected with the blood outlet manifold and exits the housing through the top or the sidewall, a gas inlet manifold, which is disposed above the oxygenator membrane and below the top of the housing and collects oxygen from a gas inlet for oxygenation of the oxygenator membrane, a gas inlet, which enters the interior of the housing through the top of the housing or the sidewall of the housing and operably connects with the gas inlet manifold, a gas outlet manifold, which is disposed below the oxygenator membrane and above the bottom of the housing and collects carbon dioxide from the oxygenator membrane, and a gas outlet, which exits the housing through the bottom or the sidewall, operably connects with the gas outlet manifold, and comprises a drain for blood or components thereof that enter the fibers of the oxygenator membrane and vent port, positioned where the air bubbles accumulate. The blood pump-oxygenator can further comprise a blood heat exchanger, in which case the blood pump-oxygenator further comprises a blood temperature probe and a temperature controller which are operably connected to the blood heat exchanger. Additionally or alternatively, the blood pump-oxygenator can further comprise a blood recirculation port or valve, which is located between the blood inlet and the blood outlet and connects the blood outlet manifold with the blood inlet, blood inlet and outlet sample ports, a blood reservoir in the interior of the housing or affixed to the exterior of the housing in operable communication with a blood outlet, and/or a blood gas sensor in operable communication with the blood inlet and an additional blood gas sensor in operable communication with the blood outlet.

The present invention also provides an extracorporeal life support system comprising the integrated centrifugal blood pump-oxygenator, a pump/motor controller, inflow and outflow cannulae and tubing, and a motor. The extracorporeal life support system can further comprise a blood flow probe connected to the pump/motor controller, a compliance chamber, between a patient to whom the extracorporeal life support system is attached and the extracorporeal life support system, a blood gas sensor and a gas supply regulator, which operably connected to the pump/motor controller, and/or a blood heat exchanger, which is positioned before the blood inlet of the blood pump-oxygenator, preferably in further combination with a blood temperature probe and a temperature controller, which are operably connected to the blood heat exchanger. When the blood pump-oxygenator comprises a blood gas sensor in operable connection with the blood inlet and an additional blood gas sensor in operable communication with the blood outlet, the system further comprises a gas supply regulator, which is operably connected to the pump/motor controller. In certain embodiments, a recirculation loop may be employed.

The present invention also provides a method of de-bubbling and priming the extracorporeal life support system. The method comprises interconnecting a tube between the blood inlet and the blood outlet and circulating a priming solution through the tube into the system, whereupon the system is de-bubbled and primed.

All references cited herein, including publications, patent applications, and patents, are hereby incorporated by reference to the same extent as if each reference were individually and specifically indicated to be incorporated by reference and were set forth in its entirety herein.

The use of the terms "a," "an", "the" and similar references in the context of describing the invention (especially in the context of the following claims) are to be construed to cover both the singular and plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood by those skilled in the art that the illustrated and described embodiments are exemplary only, and should not be taken as limiting the scope of the invention. In particular, the invention relates to all advantageous combinations of the discussed embodiments.

The invention claimed is:

1. An integrated centrifugal blood pump-oxygenator comprising a housing with
   a top having a blood inlet, a blood outlet and a gas inlet;
   a bottom having a rotational body, rotatably arranged in a rotor-housing of the bottom; and
   a substantially annular oxygenator membrane provided in an interior of the housing;
   wherein in the operation state oxygen is transferred from the gas inlet through the oxygenator membrane to a gas outlet,
   the blood pump-oxygenator being configured such that the rotational body pumps the blood from the blood inlet to an exterior surface of the oxygenator membrane, through the oxygenator membrane, to exit the oxygenator membrane at a central blood outlet channel located interior the oxygenator membrane and connected to the blood outlet.

2. An integrated centrifugal blood pump-oxygenator in accordance with claim 1, wherein the gas inlet enters the interior of the housing through the top of the housing.

3. An integrated centrifugal blood pump-oxygenator in accordance with claim 1, wherein the gas outlet exits the housing through the bottom of the housing.

4. An integrated centrifugal blood pump-oxygenator in accordance with claim 1, wherein the blood outlet exits the housing through the top of the housing.

5. An integrated centrifugal blood pump-oxygenator in accordance with claim 1, wherein the blood inlet enters the interior of the housing essentially through a center of the top of the housing.

6. An integrated centrifugal blood pump-oxygenator in accordance with claim 1, wherein the blood inlet traverses the interior of the housing, and operably connects with a frusto-conical manifold, through which, in the operating state, blood is drawn by the rotational body.

7. An integrated centrifugal blood pump-oxygenator in accordance with claim 1, wherein the bottom comprises a peripherally located, outwardly radiating diffuser blade.

8. An integrated centrifugal blood pump-oxygenator in accordance with claim 1, wherein the rotational body comprises an impeller, comprising essentially centrally located, outwardly radiating blades, wherein the impeller is disposed with respect to a manifold of the blood inlet in such a way that, in the operating state, upon rotation, blood that passes through the manifold is forced through the oxygenator membrane by the impeller.

9. An integrated centrifugal blood pump-oxygenator in accordance with claim 1, wherein the oxygenator membrane surrounds the blood inlet.

10. An integrated centrifugal blood pump-oxygenator in accordance with claim 1, wherein the oxygenator membrane comprises fibers, and at least one of an upper potting or a lower potting, wherein the potting holds the fibers in place.

11. An integrated centrifugal blood pump-oxygenator in accordance with claim 1, further comprising a blood outlet manifold, which is disposed between the oxygenator membrane and the top of the housing, wherein the blood outlet manifold is operably connected with the blood outlet, and wherein the blood outlet manifold transfers blood from the oxygenator membrane to the blood outlet in the operating state.

12. An integrated centrifugal blood pump-oxygenator in accordance with claim 1, further comprising a gas inlet manifold, which is disposed between the oxygenator membrane and the top of the housing, wherein the gas inlet manifold is operably connected with the gas inlet, and wherein the gas inlet manifold collects oxygen from the gas inlet for oxygenation of the oxygenator membrane in the operating state.

13. An integrated centrifugal blood pump-oxygenator in accordance with claim 1, further comprising a gas outlet manifold, which is disposed between the oxygenator membrane and the bottom of the housing, wherein the gas outlet manifold is operably connected with the gas outlet, and wherein the gas outlet manifold collects carbon dioxide from the oxygenator membrane in the operating state.

14. An integrated centrifugal blood pump-oxygenator in accordance with claim 1, further comprising at least one of: a recirculation loop, a blood recirculation port, or a blood recirculation valve, which is located between the blood inlet and the blood outlet and connects the blood outlet with the blood inlet.

15. An integrated centrifugal blood pump-oxygenator in accordance with claim 1, further comprising at least one of: a blood heat exchanger, a blood temperature probe, or a temperature controller.

16. An integrated centrifugal blood pump-oxygenator in accordance with claim 15, comprising the blood heat exchanger and at least one of the blood temperature probe, or the temperature controller, wherein the blood temperature probe or the temperature controller is operably connected to the blood heat exchanger.

17. An integrated centrifugal blood pump-oxygenator in accordance with claim 1, which further comprises at least one of: a blood inlet sample port or a blood outlet sample port.

18. An integrated centrifugal blood pump-oxygenator in accordance with claim 1, which further comprises a blood reservoir in the interior of the housing or affixed to an exterior of the housing, wherein the blood reservoir is in operable contact with at least one of the blood inlet and the blood outlet.

19. An integrated centrifugal blood pump-oxygenator in accordance with claim 1, which further comprises at least one of: a first blood gas sensor, which is in operable communication with the blood inlet, or a second blood gas sensor which is in operable communication with the blood outlet.

20. An integrated centrifugal blood pump-oxygenator in accordance with claim 1, wherein the blood outlet channel substantially surrounds the blood inlet.

21. An integrated centrifugal blood pump-oxygenator in accordance with claim 1, wherein the blood pump-oxygenator is further configured such that the blood flow comprises a substantially uniform flow distribution through the oxygenator membrane.

22. An integrated centrifugal blood pump-oxygenator in accordance with claim 1, wherein the blood pump-oxygenator is further configured such that the blood flow surrounds the oxygenator membrane to enter the exterior surface of the oxygenator membrane from positions distributed 360° around the oxygenator membrane.

23. An integrated centrifugal blood pump-oxygenator in accordance with claim 1, wherein the blood pump-oxygenator is further configured such that the blood flow travels from the blood inlet downwards under the influence of gravity, and is subsequently actively pushed upwards by the rotational body to the blood outlet.

24. An integrated centrifugal blood pump-oxygenator in accordance with claim 1, wherein the rotational body is magnetically journalled in a contact-free manner with respect to the rotor-housing.

25. An integrated centrifugal blood pump-oxygenator in accordance with claim 24, wherein the contact-free manner comprises a combination of active and passive magnetic suspension.

26. An integrated centrifugal blood pump-oxygenator in accordance with claim 1, wherein the gas inlet enters the interior of the housing through a sidewall of the housing.

27. An integrated centrifugal blood pump-oxygenator in accordance with claim 1, wherein the gas outlet exits the housing through a sidewall of the housing.

28. An integrated centrifugal blood pump-oxygenator in accordance with claim 1, wherein the gas outlet comprises a drain for blood or components thereof that enter a fiber of the oxygenator membrane.

29. An integrated centrifugal blood pump-oxygenator in accordance with claim 1, wherein the blood outlet exits the housing through a sidewall of the housing.

30. An extracorporeal life support system comprising an integrated centrifugal blood pump-oxygenator, the blood pump-oxygenator comprising a housing with
- a top having a blood inlet, a blood outlet and a gas inlet;
- a bottom having a rotational body, rotatably arranged in a rotor-housing of the bottom; and
- a substantially annular oxygenator membrane provided in an interior of the housing;
- wherein in the operation state oxygen is transferred from the gas inlet through the oxygenator membrane to a gas outlet,
- the blood pump-oxygenator being configured such that the rotational body pumps the blood from the blood inlet to an exterior surface of the oxygenator membrane, through the oxygenator membrane, to exit the oxygenator membrane at a central blood outlet channel located interior the oxygenator membrane and connected to the blood outlet;
- the system further comprising at least one cannula or tubing, configured to operably connect the blood pump-oxygenator to a patient.

31. An extracorporeal life support system in accordance with claim 30, further comprising a pump/motor controller operably connected to the blood pump-oxygenator.

32. An extracorporeal life support system in accordance with claim 31, further comprising a blood flow probe connected to the pump/motor controller.

33. An extracorporeal life support system in accordance with claim 31, further comprising a blood gas sensor operably connected to the pump/motor controller.

34. An extracorporeal life support system in accordance with claim 31, further comprising a gas supply regulator operably connected to the pump/motor controller.

35. An extracorporeal life support system in accordance with claim 30, further comprising a compliance chamber configured to be provided between the patient and the blood pump-oxygenator.

36. An extracorporeal life support system in accordance with claim 30, which further comprises a blood heat exchanger positioned upstream of the blood inlet of the blood pump-oxygenator.

37. An extracorporeal life support system in accordance with claim 36, which further comprises a blood temperature probe and a temperature controller, which are operably connected to the blood heat exchanger.

38. An extracorporeal life support system in accordance with claim 30, further comprising a motor configured to pump the blood through the blood pump-oxygenator.

39. An extracorporeal life support system in accordance with claim 30, wherein the at least one cannula comprises an inflow cannula and an outflow cannula, wherein the system is configured to pump the blood from the patient through the inflow cannula to the blood pump-oxygenator, and from the blood pump-oxygenator through the outflow cannula to the patient.

40. A method of de-bubbling and priming an extracorporeal life support system, the system comprising a blood pump-oxygenator which comprises a housing with
   a top having a blood inlet, a blood outlet and a gas inlet;
   a bottom having a rotational body, rotatably arranged in a rotor-housing of the bottom; and
   a substantially annular oxygenator membrane provided in an interior of the housing;
   wherein in the operation state oxygen is transferred from the gas inlet through the oxygenator membrane to a gas outlet,
   wherein the rotational body pumps the blood from the blood inlet to an exterior surface of the oxygenator membrane, through the oxygenator membrane, to exit the oxygenator membrane at a central blood outlet channel located interior the oxygenator membrane and connected to the blood outlet;
   the method comprising:
      providing the extracorporeal life support system,
      interconnecting a tube between the blood inlet and the blood outlet, and
      circulating a priming solution through the tube into the system.

41. A method, comprising:
   providing an integrated centrifugal blood pump-oxygenator comprising a housing with
      a top having a blood inlet, a blood outlet and a gas inlet;
      a bottom having a rotational body being rotatably arranged in a rotor-housing of the bottom; and
      a substantially annular oxygenator membrane provided in an interior of the housing;
   transferring oxygen from the gas inlet through the oxygenator membrane to a gas outlet; and
   pumping the blood by the rotational body from the blood inlet to an exterior surface of the oxygenator membrane, through the oxygenator membrane, to exit the oxygenator membrane at a central blood outlet channel located interior the oxygenator membrane and connected to the blood outlet.

42. A method in accordance with claim 41, wherein pumping the blood through the oxygenator membrane comprises pumping the blood with a substantially uniform blood flow distribution through the oxygenator membrane.

43. A method in accordance with claim 41, wherein pumping the blood comprises pumping the blood to surround the oxygenator membrane such that the blood flow enters the exterior surface of the oxygenator membrane from positions distributed 360° around the oxygenator membrane.

44. A method in accordance with claim 41, wherein the blood flow travels from the blood inlet downwards under the influence of gravity, and is subsequently actively pushed upwards by the pumping of the rotational body to the blood outlet.

45. A method in accordance with claim 41, wherein the rotational body is magnetically journalled in a contact-free manner with respect to the rotor-housing.

46. A method in accordance with claim 45, wherein the contact-free manner comprises a combination of active and passive magnetic suspension.

47. A method of reducing hyper- and hypo-perfusion of blood comprising the following steps:
   providing an extracorporeal life support system comprising an integrated centrifugal blood pump-oxygenator, the blood pump-oxygenator comprising a housing with
      a top having a blood inlet, a blood outlet and a gas inlet;
      a bottom having a rotational body, rotatably arranged in a rotor-housing of the bottom; and
      a substantially annular oxygenator membrane provided in an interior of the housing;
      wherein in the operation state oxygen is transferred from the gas inlet through the oxygenator membrane to a gas outlet,
      the blood pump-oxygenator being configured such that the rotational body pumps the blood from the blood inlet to an exterior surface of the oxygenator membrane, through the oxygenator membrane, to exit the oxygenator membrane at a central blood outlet channel located interior the oxygenator membrane and connected to the blood outlet; and
   pumping the blood through the life support system.

* * * * *

UNITED STATES PATENT AND TRADEMARK OFFICE
CERTIFICATE OF CORRECTION

PATENT NO. : 8,496,874 B2
APPLICATION NO. : 11/999707
DATED : July 30, 2013
INVENTOR(S) : Gellman et al.

It is certified that error appears in the above-identified patent and that said Letters Patent is hereby corrected as shown below:

In the Specification

Column 1, lines 15-21, delete "This work was supported, at least in part, by the National Institutes of Health Small Business Technology Transfer under Grant No. NIH 5R42 HL084807. Therefore, the Government of the United States of America has certain rights in the invention."

and insert --This invention was made with government support under Grant Number HL084807 awarded by the National Institutes of Health. The government has certain rights in the invention.--

Signed and Sealed this
Nineteenth Day of November, 2013

Teresa Stanek Rea
*Deputy Director of the United States Patent and Trademark Office*